United States Patent [19]

Upsher

[11] Patent Number: 5,651,761
[45] Date of Patent: Jul. 29, 1997

[54] LARYNGOSCOPE INCLUDING AN ENDOTRACHEAL TUBE SEPARATION MOUTH AND ITS METHOD OF USE

[75] Inventor: Michael S. Upsher, Menlo Park, Calif.

[73] Assignee: Upsher Laryngoscope Corp., Foster City, Calif.

[21] Appl. No.: 426,214

[22] Filed: Apr. 21, 1995

[51] Int. Cl.⁶ ................................................ A61B 1/267
[52] U.S. Cl. ................................... 600/194; 600/190
[58] Field of Search ........................ 600/185, 190–194, 600/196–199, 120

[56] References Cited

U.S. PATENT DOCUMENTS

| | | | |
|---|---|---|---|
| 4,306,547 | 12/1981 | Lowell | 600/194 |
| 4,437,458 | 3/1984 | Upsher | 600/193 |
| 4,832,020 | 5/1989 | Augustine | 600/194 |
| 5,065,738 | 11/1991 | VanDam | 600/185 |
| 5,443,058 | 8/1995 | Ough | 600/190 X |

*Primary Examiner*—Richard J. Apley
*Assistant Examiner*—David R. Risley
*Attorney, Agent, or Firm*—Stephen C. Shear

[57] ABSTRACT

An improved laryngoscope and its method of use are disclosed herein. The laryngoscope includes a handle and a blade which defines a slot along its length. A tube separation mouth, which is widened in comparison to the slot and which leads into the slot, is provided integral with an uppermost portion of the blade for use during separation of an intubated endotracheal tube from the blade.

In a method of separating the blade from an intubated tube, the tube is moved into the separation mouth and thereafter into the slot. The tube is then passed down the slot to be released therefrom as the blade is withdrawn from the throat of the patient.

12 Claims, 4 Drawing Sheets

LARYNGOSCOPE INCLUDING AN ENDOTRACHEAL TUBE SEPARATION MOUTH AND ITS METHOD OF USE

BACKGROUND OF THE INVENTION

The present invention relates generally to a laryngoscope, and more particularly to a laryngoscope including a separation mouth used in separating an intubated tube from the laryngoscope blade while removing the laryngoscope from a patient's throat.

The use of a laryngoscope for the intubation of a patient, as well as its use in other procedures, is well known in the art. FIGS. 1–4 illustrate a typical prior art laryngoscope, generally indicated by reference numeral 10. Laryngoscope 10 includes a handle 12 and a tubular blade 14 which are disengagably connectable to one another.

Referring specifically to FIGS. 1 and 2, blade 14 includes an uppermost handle connecting end 16 and a tongue engaging end 18. The blade includes a tube passage 20 which extends from the handle connecting end to the tongue engaging end of the blade. Tube passage 20 has an entrance opening 22 at the handle connecting end of the blade and an exit opening 24 at the tongue engaging end of the blade. A slot 26 having a width 28 extends along an outer margin of the blade from handle connecting end 16 to tongue engaging end 18.

Referring now to FIG. 3, which shows an intubation procedure in progress, blade 14 of the laryngoscope is positioned in the throat of a patient 29. A flexible endotracheal tube 30 having a deformable diameter 32 has been inserted into entrance opening 22 of the tubular blade, passed through tube passage 20 and positioned in the trachea of patient 29. The diameter of tube 30 is slightly less than the width of tube passage 20 so that the tube is slidably received within the blade, but, at the same time, the diameter of the tube is substantially greater than width 28 of slot 26. Since diameter 32 of tube 30 in an undeformed condition is greater than width 28 of slot 26, the tube is retained within the tube passage as it is passed down from handle connecting end 16 to tongue engaging end 18 to be positioned in the patient's trachea, as shown. Once the tube is positioned it is separated from the blade, which will be described immediately hereinafter.

FIG. 4 illustrates the beginning of the procedure which must be carried out in order to remove the tube from the blade, while leaving the tube intubated in the patient apart from the laryngoscope. The tube must be deformed along its diameter at point 33 until the deformed diameter is approximately equal to width 28 of the slot. At this point the tube, while continuing to be deformed, is forced into the slot at handle connecting end 16 of the blade. This may be accomplished by squeezing the tube with a hand or a suitable instrument while forcing the tube into the slot. To complete the separation of the tube from the blade, which is not illustrated here, the tube is simply passed along the length of the slot while being deformed by the slot until it reaches the tongue engaging end of the blade where it is released from the slot, while withdrawing the blade from the patient. This may require the simultaneous removal of the blade by sliding the blade off the tube.

While the prior art laryngoscope, as depicted in FIGS. 1–4, is generally satisfactory for its intended purpose, there is a particular aspect of the instrument as shown and described above which may be improved upon in accordance with the present invention, as will be discussed below.

As described above, the tube must be deformed along its diameter in order for it to be inserted into the slot to begin the separation of the tube from the blade. This can be difficult to accomplish during a procedure, especially when a health care professional may be involved in many other important aspects of the procedure being performed.

As will be seen hereinafter, the present invention provides a laryngoscope including a unique feature and method for inserting the tube into the slot which requires no more than minimal deformation of the tube by the health care professional prior to its insertion into the slot.

SUMMARY OF THE INVENTION

As will be described in more detail hereinafter, a laryngoscope and method of using it are herein disclosed. This laryngoscope, like the prior art laryngoscope shown in FIGS. 1–4, includes a handle and a blade having a slot for separating the blade from an intubated tube. However, in accordance with the present invention, the laryngoscope disclosed herein includes a proximate end of the blade defining a separation mouth which has a width greater than the width of the slot and which leads into the slot to accommodate removal of the tube from the tube guiding portion by first passing the tube through the separation mouth and thereafter into the slot while separating the blade from the tube to leave the tube in an intubated state within the patient after removal of the laryngoscope from the patient.

In a method of using the laryngoscope of the present invention during a procedure, in which the blade includes a proximate end, a tube guiding portion and a slot defined by the tube guiding portion along its length, the method includes the steps of: inserting the blade into the patient, guiding the tube from the proximate end of the blade through the tube guiding portion into the trachea of the patient, providing a separation mouth at the proximate end of the blade which is wider than the slot and which leads into the slot defined along the length of the tube guiding portion of the blade, moving the tube into the separation mouth and thereafter into the slot and passing the tube through the slot while removing the laryngoscope from the patient until the tube is released from slot at the tongue engaging end of the blade.

BRIEF DESCRIPTION OF THE DRAWINGS

The present invention may be understood by reference to the following detailed description taken in conjunction with the drawings, in which.

DETAILED DESCRIPTION OF THE INVENTION

Figure 1:
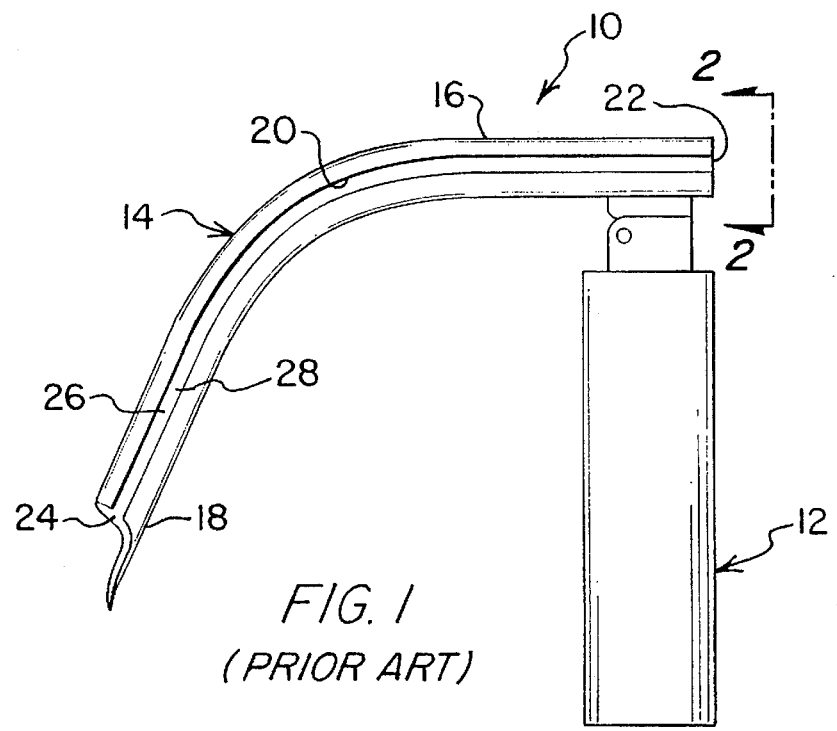
FIG. 1 illustrates a prior art laryngoscope including a blade having a slot extending along its length.
Figure 2:
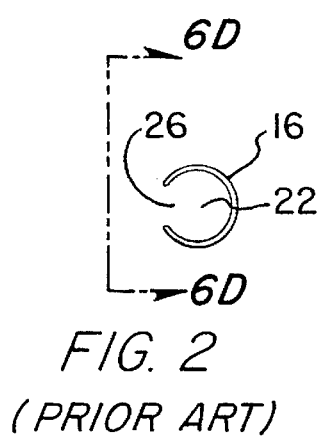
FIG. 2 is an elevational end view of the handle connecting end of the blade of the laryngoscope which is illustrated in FIG. 1.
Figure 3:
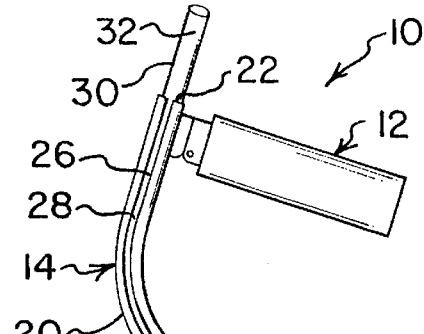
FIG. 3 is an illustration of the laryngoscope of FIGS. 1 and 2 in use during an intubation procedure.
Figure 3:
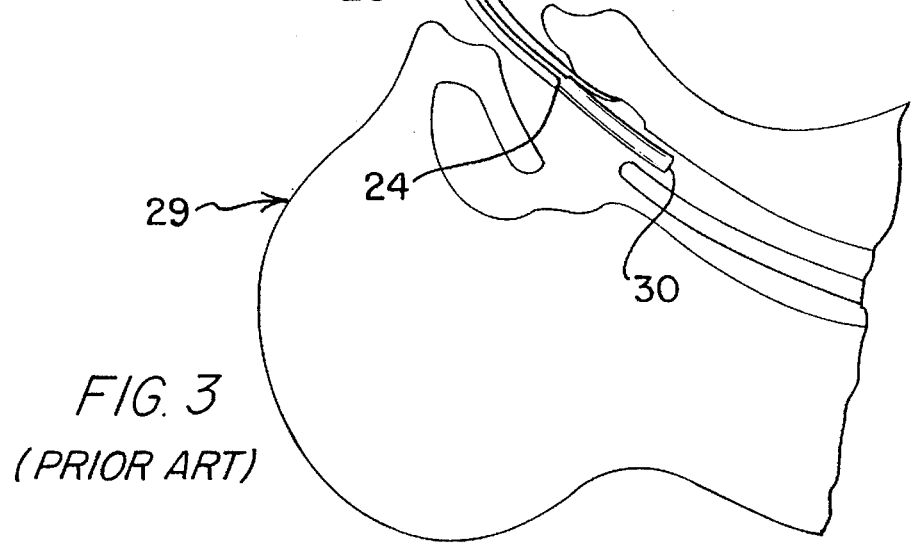
Figure 4:
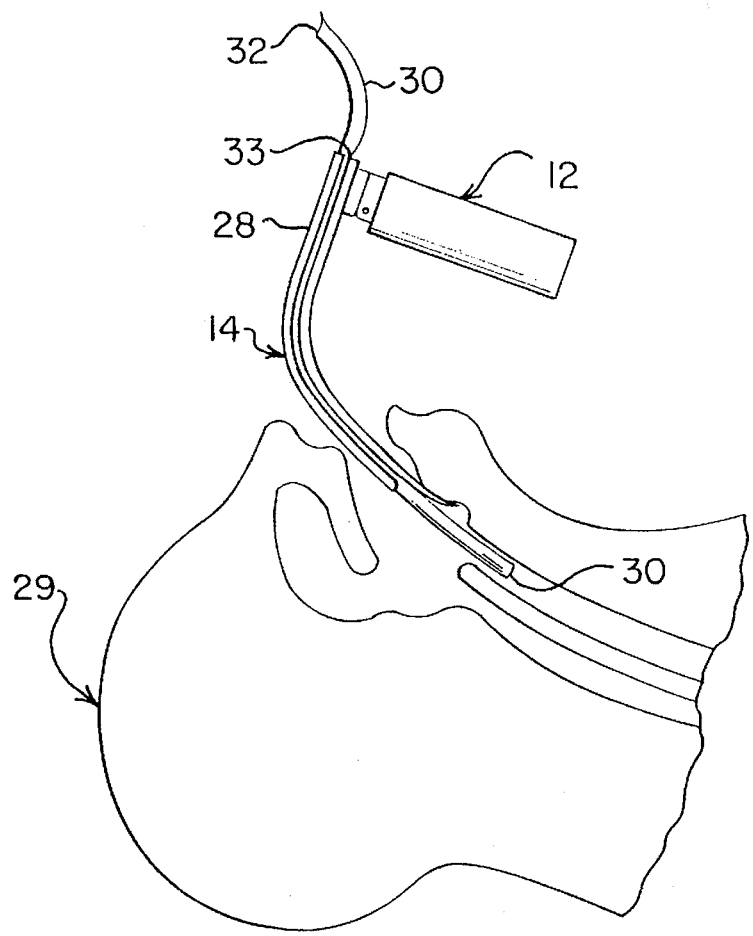
FIG. 4 depicts a later step in the procedure shown in FIG. 3 in which the intubated tube is being separated from the laryngoscope blade.
Figure 5:
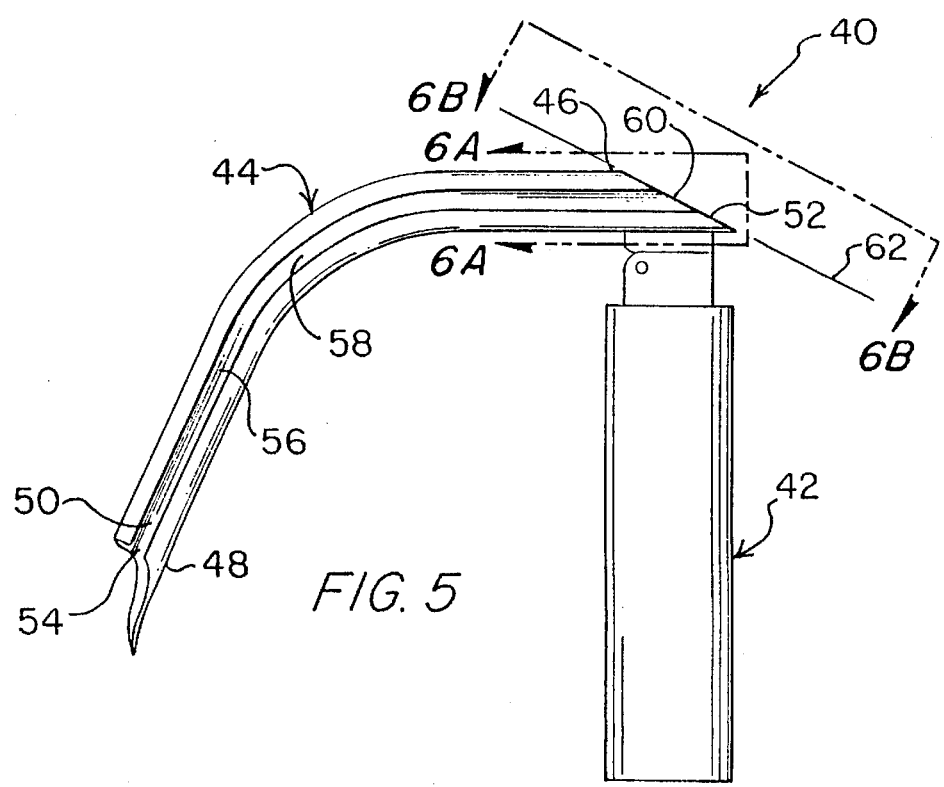
FIG. 5 is a side elevational view of a laryngoscope manufactured in accordance with the present invention showing a widened separation mouth leading into the slot at the proximate end of the blade.

Having described FIGS. 1 through 4 previously, attention is immediately directed to FIG. 5, which illustrates a laryngoscope manufactured in accordance with the present invention and generally designated by reference numeral 40. Laryngoscope 40 includes a handle 42 and a blade 44. The blade, as shown, is curved, but the invention disclosed herein is useful with blades of varying curvature or, in fact, no curvature. The blade includes an handle connecting end 46 which is disengagably connectable with the handle, as is shown in FIG. 5, although the handle may be connected to the blade by any other suitable arrangement, such as fixing the handle directly in its operating position on the blade, without affecting the utility of the invention disclosed herein. The laryngoscope of the present invention may incorporate any other feature of state of the art laryngoscopes, for example, such as remote viewing and lighting features. These features are not illustrated herein for simplicity.

Figure 6A:
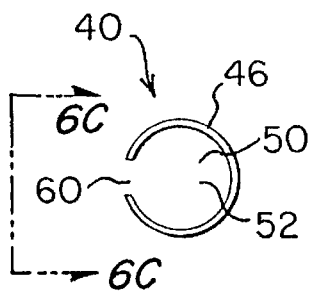
FIG. 6A is an handle connecting end view of the blade of the laryngoscope which is illustrated in FIG. 5.

Referring now to FIG. 6A in conjunction with FIG. 5, blade 44 includes a tongue engaging end 48. The blade also includes a tube passage 50 which extends from handle connecting end 46 to tongue engaging end 48 of the blade. Generally, tube passage 50 is circular in cross-section, but other shapes, for example, such as elliptical, may be found to be useful. Tube passage 50 includes an entrance opening 52 at the handle connecting end of the blade and an exit opening 54 at the tongue engaging end of the blade. A slot 56 having a width 58 extends along a side margin of the blade from handle connecting end 46 to tongue engaging end 48. The slot may actually be defined on any available portion of the outer portion of the blade to be useful with the present invention and is shown here positioned on a side margin of the blade as a matter of example only.

Figure 6B:
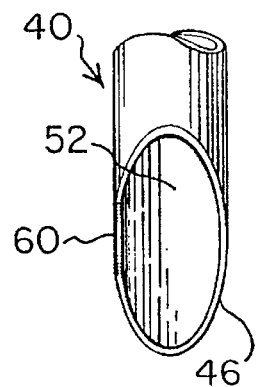
FIG. 6B is a fragmentary end view of the blade of the laryngoscope of the present invention which is taken in a plane parallel to the separation mouth.

In accordance with a preferred embodiment of the present invention and illustrated in FIGS. 5 and 6A-C, a separation mouth 60 is provided at entrance opening 52 of handle connecting end 46 of the blade. The separation mouth forms a widened opening in relationship to width 58 of slot 56 and actually comprises the entrance of the slot. In the present example, the separation mouth is formed by beveling uppermost portion 46 of the blade in a plane 62 which diagonally bisects slot 56. FIG. 6B is a view of the beveled end of the blade taken in a plane which is parallel to the plane of the bevel. Separation mouth 60 is clearly visible as being considerably widened in comparison to width 58 of the slot, as shown in FIG. 6A. When the separation mouth is formed in this manner, the angle of the bevel directly determines the width of the mouth and the width may be varied in the manufacture of the blade by simply altering the angle of bevel taken on the blade.

Figure 6C:
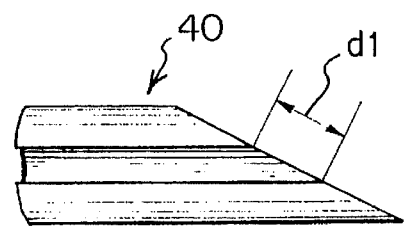
FIG. 6C is a fragmentary side elevational view of the handle connecting end of the blade of the laryngoscope blade which is shown in FIG. 6A to illustrate the widened separation mouth of the present invention.
Figure 6D:
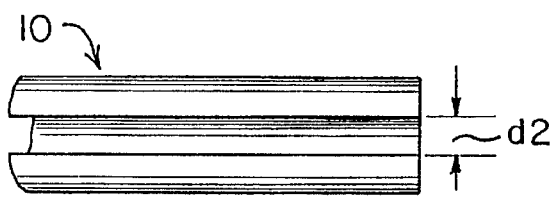
FIG. 6D is a fragmentary side elevational view of the handle connecting end of the prior art laryngoscope blade which is shown in FIG. 2 and is illustrated here for direct comparison with the laryngoscope blade of the present invention as shown in FIG. 6C.

Turning now to adjacent FIGS. 6C and 6D, wherein a direct comparison of the width of the separation mouth of the laryngoscope of the present invention is made to the width of the separation mouth of the prior art laryngoscope. FIG. 6C is a side view of the laryngoscope of the present invention in which the width of the separation mouth is represented as d1. FIG. 6D, on the other hand, is a side view of the separation mouth of the prior art laryngoscope (shown also in FIGS. 1 and 2) in which the width of the separation mouth is represented as d2. Comparison of d1 to d2 clearly shows that d1 is significantly greater than d2, thus providing a widened separation mouth, in accordance with the present invention. The advantage provided by the widened separation mouth of the laryngoscope of the present invention lies in its method of use, which will be discussed immediately hereinafter.

Figure 7:
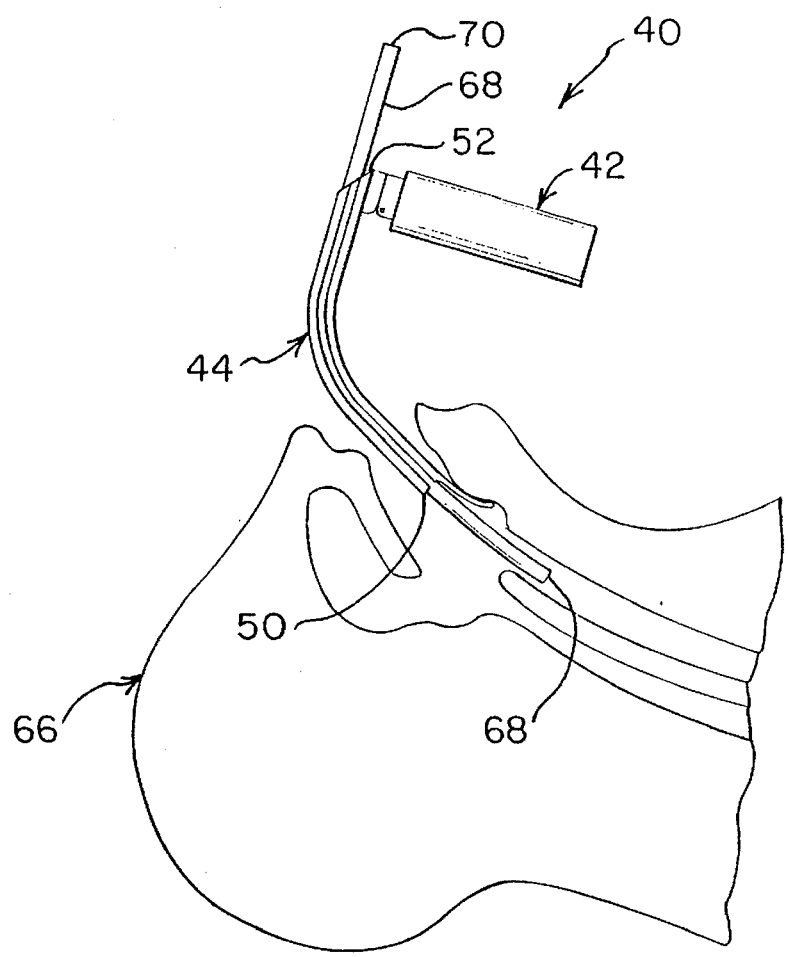
FIG. 7 is an illustration of the laryngoscope which is shown in FIGS. 5 and 6 in use during an intubation procedure.

During an intubation procedure, which is illustrated in FIG. 7, blade 44 of the laryngoscope is positioned in the throat of a patient 66. An endotracheal tube 68 including a deformable diameter 70 is inserted into opening 52 of the blade. The diameter of tube 68 is slightly less than the width of tube passage 50 such that the tube is slidably receivable within the blade, but, at the same time, the undeformed diameter of the tube is substantially greater than width 58 of slot 56, as was the case with the prior art laryngoscope in the discussion above. Tube 68 is also flexible in order to bend sufficiently to follow the curvature of the blade as it is inserted in the latter. The requirements for both flexibility and a deformable diameter are fulfilled by currently available endotracheal tubes.

Still referring to FIG. 7, it can be seen that tube 68 has already been passed through tube passage 50 and is positioned within the trachea of the patient. Since diameter 70 of the tube, when undeformed, is greater than width 58 of the slot, the tube is retained within the tube passage while it is being passed therethrough for placement, as shown, within the patient's trachea. Once the tube is properly positioned, it may then be separated from the blade.

Figure 8:
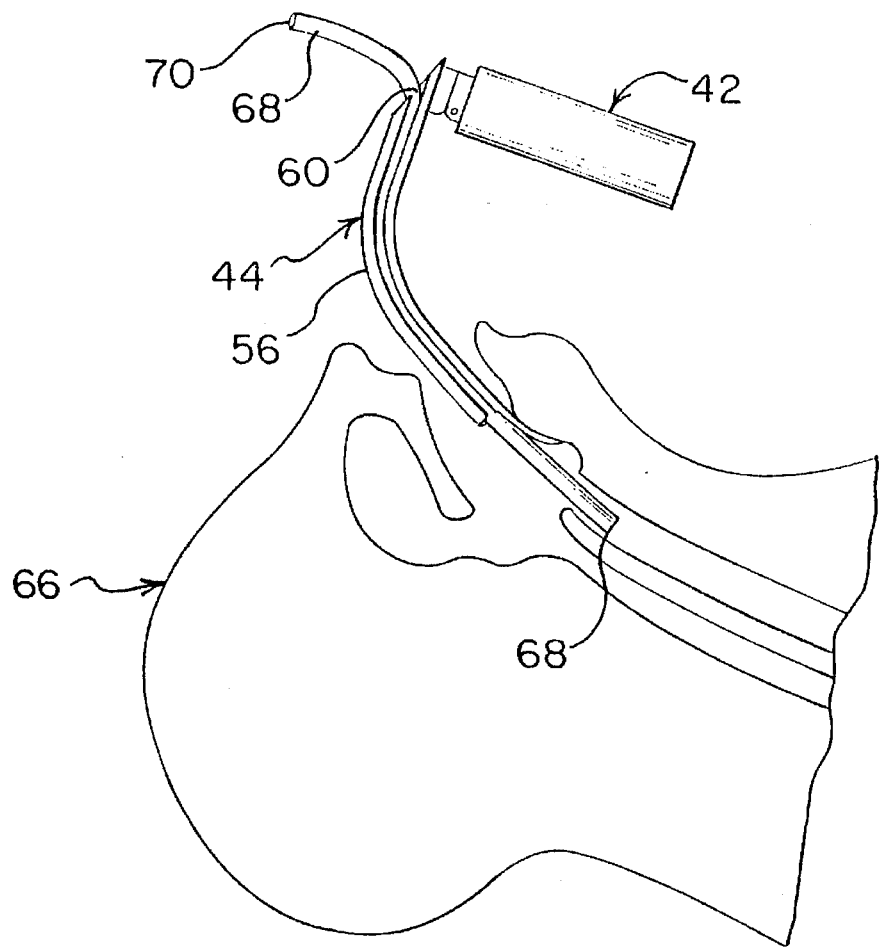
FIG. 8 depicts a later step in the procedure shown in FIG. 7 in which the intubated tube is being separated from the laryngoscope blade using a feature of the present invention.

In accordance with the present invention, and illustrated in FIG. 8, tube 68 is separated from the blade by the method of first positioning the tube in separation mouth 60. Since the separation mouth is substantially wider than slot 56, tube 68 may be inserted into the separation mouth with little deformation of the tube required and, in some cases, dependent upon the width of the separation mouth, as defined by the geometry of handle connecting end 46 of the blade, and diameter 70 of the tube, the separation mouth may actually be wider than the diameter of the tube to permit diameter 70 of the tube to be received within the separation mouth undeformed. In either case, the tube is easily positioned in the separation mouth, since the latter is substantially wider than the width of the slot. After the tube is positioned in the separation mouth, it is passed into slot 56 by deforming it along diameter 70 until it is received within the slot. This may be accomplished by simply pressing the tube into the slot after it is received by the separation mouth (not shown).

To complete the separation of the tube from the blade (not shown), the tube is then moved along the slot, in the manner of the prior art, to be released from the blade at tongue engaging end 48 of the blade while the blade is being withdrawn from the patient's throat.

Figure 9:
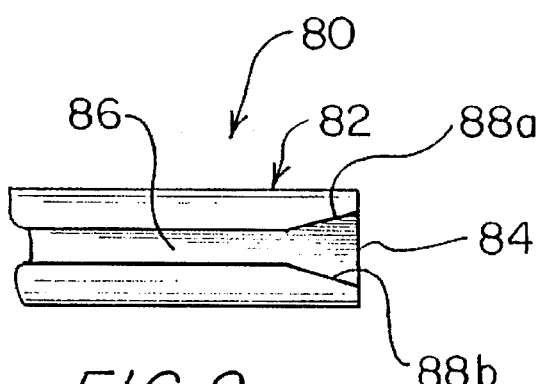
FIG. 9 is a fragmentary side elevational view of an alternative configuration for the handle connecting end of the blade of a laryngoscope manufactured in accordance with the present invention including a widened separation mouth.

As described previously, the widened separation mouth of the present invention was achieved by an oblique bevel where the slot is of a uniform width throughout its extent. It is equally applicable, although not as preferred, to simply or in combination provide an enlarged end section in the slot to form a widened separation mouth. FIG. 9 is a fragmentary side view of a laryngoscope blade (the remainder of the laryngoscope is not shown here for simplicity) generally designated by reference numeral 80. Blade 80 includes an handle connecting end 82 having a widened separation mouth 84 which leads into a slot 86. In this alternative embodiment of the invention, slot 86 includes opposing diverging edge portions 88a and 88b which lead to separation mouth 84.

The separation mouth may be formed by an unlimited variety of geometries at the uppermost portion of the blade other than the particular forms which are specifically illustrated herein, for example, in the case where the blade is beveled, as described in the preferred embodiment, the bevel may be carried through only an outermost portion of the blade or the blade may be asymmetrically cut away, as opposed to a bevel carried out in a plane. All of these geometries are considered to be within the scope of the present invention, provided only that the separation mouth is wider than the width of the slot.

The laryngoscope of the present invention may be produced from a variety of materials, for example, such as stainless steel or suitable plastics which may even provide a degree of flexibility in the blade. Plastic embodiments may also be of a disposable type. It is also anticipated that blades incorporating the features of the present invention may be provided which are adaptable for use with various prior art laryngoscope handles, which are currently in use, to provide the advantages herein disclosed.

Since a separation mouth for separating a laryngoscope blade from an intubated tube may be provided using a variety of blade orientations and geometries, it should be understood that the present invention may be embodied in many other specific forms without departing from the spirit or scope of the invention. Therefore, the present examples and methods are to be considered as illustrative and not restrictive, and the invention is not to be limited to the details given herein, but may be modified within the scope of the appended claims.

What is claimed is:

1. A laryngoscope for intubating a patient with a tube, said laryngoscope comprising:
   a) a handle; and
   b) a blade extending from said handle, said blade including
      i. a distal end, a proximate end engaging said handle and a length defined therebetween,
      ii. a tube guiding portion configured to receive and route said tube from said proximate end to said distal end along said length, said tube guiding portion defining a slot of a predetermined width along the length of the blade;
      iii. said proximate end of the tube guiding portion having an oblique surface which lies in a plane that obliquely cuts through the slot forming a separation mouth at the entrance of the slot the separation mouth being wider than the slot so as to accommodate removal of the blade from the tube by first passing the tube through the separation mouth and thereafter into the slot while separating the blade from the tube whereby to leave the tube in an intubated state within the patient after removal of the laryngoscope from the patient.

2. A laryngoscope in accordance with claim 1 wherein the blade is disengagably connectable to the handle.

3. A laryngoscope in accordance with claim 1 wherein said tube is deformable and has an undeformed diameter which is larger than the width of the slot such that the tube can be passed through the separation mouth with minimal deformation and is squeezed or otherwise deformed by the slot in a way which reduces its diameter as the tube passes through the slot in separating the tube from the blade.

4. A laryngoscope in accordance with claim 1 wherein said tube is deformable and has an undeformed diameter which is larger than the width of the slot and wherein said width of said separation mouth is larger than the undeformed diameter of the tube such that the tube can be passed through the separation mouth undeformed and is squeezed or otherwise deformed by the slot in a way which reduces its diameter as the tube passes through the slot in separating the tube from the blade.

5. A laryngoscope in accordance with claim 1 wherein a portion of the proximate end of the tube guiding portion is beveled to form the separation mouth such that the latter is wider than the slot.

6. A laryngoscope in accordance with claim 1 wherein the blade is disengagably connectable with the handle.

7. A laryngoscope for intubating a patient with a tube having a deformable diameter, said laryngoscope comprising:
   a) a handle; and
   b) a blade extending from said handle, said blade including
      i. a distal end, a proximate end engaging said handle and a length defined therebetween,
      ii. a tube guiding portion configured to receive and route said tube from said proximate end to said distal end along said length, said tube guiding portion including a pair of opposing edges defining a slot of a predetermined width which is smaller than the predetermined diameter of the tube along the length of the blade;
      iii. said proximate end of the tube guiding portion having an oblique surface which lies in a plane that obliquely cuts through the slot forming a separation mouth at the entrance of the slot, the separation mouth being wider than the, slot so as to accommodate separation of the tube from the tube guiding portion by first passing the tube through the separation mouth with minimal or no deformation of the tube and thereafter into the slot such that said deformable diameter is squeezed or otherwise deformed by the opposing edges of the slot in separating the tube from the blade while removing the blade from the patient's throat whereby to leave the tube in an intubated state within the patient after removal of the laryngoscope from the patient.

8. A method of intubating a patient with a tube using a laryngoscope including a handle and a blade, said blade including a proximate end and a tube guiding portion, said method including the steps of:
   a) inserting the blade into said patient;
   b) guiding said tube from said proximate end through the tube guiding portion of the blade into the trachea of the patient;

c) providing a slot which is defined along the length of the tube guiding portion of the blade;

d) providing an oblique surface at the proximate end of the blade which obliquely cuts through the slot forming a separation mouth at the entrance of the slot, the separation mouth being wider than the slot; and e) separating the tube from the tube guiding portion by first moving the tube through the separation mouth and thereafter into the slot while removing the laryngoscope from the patient.

9. A method according to the method of claim 8 wherein said tube includes a deformable diameter which is larger than the width of the slot and the method includes the step of squeezing or otherwise deforming the tube as it enters the slot after passing through the separation mouth with minimal or no deformation.

10. A blade for use in intubating a patient with a tube as part of a laryngoscope which also includes a handle having a blade engaging segment, said blade comprising:

a) a distal end, a proximate end engaging said handle and a length defined therebetween;

b) a tube guiding portion configured to receive and route said tube from said proximate end to said distal end along said length;

c) a slot having a predetermined width defined by said tube guiding portion along the length of the blade; and d) an oblique surface at the proximate end of said blade which obliquely cuts through said slot forming a separation mouth at the entrance of the slot such that the width of the separation mouth is greater than the width of the slot to accommodate separation of the tube from the tube guiding portion through the slot by first passing the tube through the separation mouth and into the slot in separating the tube from the blade while removing the blade from the patient's throat whereby to leave the tube in an intubated state within the patient after removal of the tube from the laryngoscope.

11. A blade in accordance with claim 10 wherein said tube is deformable and has an undeformed diameter which is larger than the width of the slot such that the tube can be passed through the separation mouth with minimal deformation and is squeezed or otherwise deformed by the slot in a way which reduces its diameter as the tube passes through the slot in separating the tube from the blade.

12. A blade in accordance with claim 10 wherein said tube is deformable and has an undeformed diameter which is larger than the width of the slot and wherein said width of said separation mouth is larger than the undeformed diameter of the tube such that the tube can be passed through the separation mouth undeformed and is squeezed or otherwise deformed by the slot in a way which reduces its diameter as the tube passes through the slot in separating the tube from the blade.

* * * * *